(12) United States Patent
Boulter (10) Patent No.: US 12,241,840 B2
(45) Date of Patent: Mar. 4, 2025

(54) REAL-TIME SILICA DISCRIMINATING RESPIRABLE AEROSOL MONITOR WITH PARTICLE SIZER AND PARTICLE GROWTH CHAMBER UPSTREAM OF REAGENT TANK

(71) Applicant: WiSys Technology Foundation, Inc., Madison, WI (US)

(72) Inventor: James E. Boulter, Eau Claire, WI (US)

( * ) Notice: Subject to any disclaimer, the term of this patent is extended or adjusted under 35 U.S.C. 154(b) by 470 days.

(21) Appl. No.: 16/379,263

(22) Filed: Apr. 9, 2019

(65) Prior Publication Data

US 2019/0310202 A1 Oct. 10, 2019

Related U.S. Application Data

(60) Provisional application No. 62/654,713, filed on Apr. 9, 2018.

(51) Int. Cl.
*G01N 21/76* (2006.01)
*G01N 21/85* (2006.01)
*G01N 33/00* (2006.01)

(52) U.S. Cl.
CPC ........... *G01N 21/766* (2013.01); *G01N 21/85* (2013.01); *G01N 33/0036* (2013.01); *G01N 33/0062* (2013.01); *G01N 33/0073* (2013.01); *G01N 2021/8578* (2013.01); *G01N 33/0068* (2024.05); *G01N 2201/126* (2013.01)

(58) Field of Classification Search
CPC .. G01N 21/766; G01N 21/85; G01N 33/0062; G01N 33/0073; G01N 33/0036
USPC ........................................ 422/88, 91; 436/72
See application file for complete search history.

(56) References Cited

U.S. PATENT DOCUMENTS 2,549,574 A * 4/1951 Condiff .................. G01N 21/64 356/246
2,795,819 A * 6/1957 Lord ......................... B22F 9/14 241/1
3,070,990 A * 1/1963 Krinov ................. G01N 1/2202 73/23.31
3,434,977 A * 3/1969 Neugebauer ......... B01J 13/0086 252/1
3,494,217 A * 2/1970 Tatsuo ............... G01N 15/0255 73/865.5
3,690,837 A * 9/1972 Witz ...................... G01N 21/76 422/52
3,759,617 A * 9/1973 Barringer ............. G01N 1/2211 356/36
3,823,602 A * 7/1974 Anderson ............ G01N 1/2211 73/865.5

(Continued)

FOREIGN PATENT DOCUMENTS

JP 2015-64269 * 4/2015
WO 2016/147098 * 9/2016

OTHER PUBLICATIONS

Foster, R. D. et al, Analyst 1984, 109, 1117-1127.*

(Continued)

*Primary Examiner* — Arlen Soderquist
(74) *Attorney, Agent, or Firm* — Boyle Fredrickson, S.C.

(57) ABSTRACT

An airborne silica detection system provides a chemiluminescence reaction for quantitative assessment of silica on an automated basis. A prefilter allows reaction to be sensitive to particle sizes relevant to chronic respiratory diseases.

16 Claims, 3 Drawing Sheets

(56) References Cited

U.S. PATENT DOCUMENTS

| | | | | |
|---|---|---|---|---|
| 3,970,428 | A * | 7/1976 | Barringer | G01V 9/007 73/863.22 |
| 4,178,794 | A * | 12/1979 | Jugle | G01N 1/2202 55/467 |
| 4,329,316 | A * | 5/1982 | Wladimiroff | G01N 21/76 422/52 |
| 4,350,507 | A * | 9/1982 | Greenough | G01N 1/2205 55/482 |
| 4,526,678 | A * | 7/1985 | Myhren | B04C 9/00 373/9 |
| 4,652,520 | A * | 3/1987 | Bauman | G01N 33/552 422/400 |
| 4,941,899 | A * | 7/1990 | Liu | G01N 1/2211 55/337 |
| 5,078,759 | A * | 1/1992 | Kira | B01D 47/021 261/121.1 |
| 5,110,553 | A * | 5/1992 | Ruschak | G01N 1/20 422/68.1 |
| 5,725,634 | A * | 3/1998 | Takasuga | G01N 1/2214 95/149 |
| 6,054,324 | A * | 4/2000 | Sullivan | G01N 1/34 435/31 |
| 6,447,574 | B1 * | 9/2002 | Frier, Jr. | B01D 47/10 261/116 |
| 6,506,345 | B1 * | 1/2003 | Lee | G01N 15/0255 422/68.1 |
| 6,532,835 | B1 * | 3/2003 | Saaski | G01N 1/2273 73/863.21 |
| 7,390,339 | B1 * | 6/2008 | Warrick | B04C 5/13 96/417 |
| 8,309,029 | B1 * | 11/2012 | Wick | G01N 15/065 422/50 |
| 2003/0077690 | A1 * | 4/2003 | Eden | C12Q 1/04 435/6.12 |
| 2003/0082825 | A1 * | 5/2003 | Lee | G01N 15/0255 436/148 |
| 2003/0194816 | A1 * | 10/2003 | Wakamatsu | G01N 33/0011 436/175 |
| 2004/0038385 | A1 * | 2/2004 | Langlois | G01N 1/2202 435/287.1 |
| 2006/0110818 | A1 * | 5/2006 | Hill | G01N 15/06 435/287.1 |
| 2007/0231217 | A1 * | 10/2007 | Clinton | G01N 35/1079 422/119 |
| 2011/0159596 | A1 * | 6/2011 | Keinan | G01N 1/2211 436/52 |
| 2014/0083167 | A1 * | 3/2014 | Liu | G01N 5/02 73/28.02 |
| 2014/0260542 | A1 * | 9/2014 | Nagano | G01N 1/2211 73/28.04 |
| 2015/0068806 | A1 * | 3/2015 | Duran Toro | E21B 49/00 175/50 |
| 2016/0116390 | A1 * | 4/2016 | Tan | G01N 1/2211 73/28.04 |
| 2016/0129478 | A1 * | 5/2016 | Geertsen | C01B 33/02 209/11 |
| 2017/0320745 | A1 * | 11/2017 | Geertsen | B07B 1/22 |
| 2017/0370809 | A1 * | 12/2017 | Miller-Lionberg | G01N 1/2202 |

OTHER PUBLICATIONS

Chow, J. C., Journal of the Air & Waste Management Association 1995, 45, 320-382.*
Yabuta, J. et al, Industrial Health 2003, 41, 249-259.*
Yaqoob, M. et al, Analytica Chimica Acta 2004, 519, 137-142.*
Oh, S. et al, Journal of Aerosol Science 2010, 41, 889-894.*
Brown, J. S. et al, Particle and Fibre Toxicology 2013, 10, paper 12, 12 pages.*
Edu, O. et al, Journal of Nanotechnology and Nanomaterials 2015, 4, paper 2, 6 pages.*
Hozdic, C., Analytical Chemistry 1966, 38, 1626-1627.*
Kumar, V. et al, Atmospheric Environment 1991, 25A, 1033-1038.*
Giacomelli, M. C. et al, Analytica Chimica Acta 1999, 396, 285-292.*
Kim, S. et al, Aerosol Science 2001, 32, 1281-1297.*
Jantunen, M. et al, Chemosphere 2002, 49, 993-1007.*
Lee, T. et al, Annals of Occupational Hygiene 2010, 54, 697-709.*
McDevitt, J. J. et al, Aerosol Science and Technology 2013, 47, 444-451.*
Verpaele, S. et al, Annals of Occupational Hygiene 2013, 57, 54-62.*
Wang, D. et al, Aerosol Science and Technology 2013, 47, 1226-1238.*
Mischler, S. E. et al, Journal of Occupational and Environmental Hygiene 2013, 10, 685-693.*
Garcia, A. et al, Journal of Occupational and Environmental Hygiene 2014, 11, D200-D207.*
Pan, M. et al, Journal of Applied Microbiology 2016, 120, 805-815.*
Gupta, T. et al, Inhalation Technology 2004, 16, 851-862.*
Sorooshian, A. et al, Aerosol Science and Technology 2008, 42, 445-464.*
Hering, S. V. et al, Aerosol Science and Technology 2014, 48, 401-408.*
Weber, R. J. et al, Aerosol Science & Technology 2001, 35, 718-727. (Year: 2001).*
Orsini, D. A. et al, Atmospheric Environment 2003, 37, 1243-1259. (Year: 2003).*
Sullivan, A. P. et al, Geophysical Research Letters 2004, 31, paper L13105, 4 pages. (Year: 2004).*
Glagolenko, S. et al, Journal of Geophysical Research 2004, 109, paper D18205, 12 pages. (Year: 2004).*
Tsai, C.-J. et al, Environmental Science & Technology 2012, 46, 4546-4552. (Year: 2012).*
Akbar-Khanzadeh, F. et al, Journal of Occupational and Environmental Hygiene 2012, 9, 502-516. (Year: 2012).*
Fahnoe, F. et al, Industrial and Engineering Chemistry 1951, 43, 1336-1346. (Year: 1951).*
Whong, W.-Z. et al, Mutation Research 1984, 130, 45-51. (Year: 1984).*
Ong, T.-M. et al, in Short-Term Bioassays in the Analysis of Complex Environmental Mixtures IV Waters, M. D. et al, editors, Springer Science+Business Media, New York, 1985, 25-36. (Year: 1985).*
Kim, D. S. et al, Journal of Korean Society for Atmospheric Environment 2008, 24, 24-31. (Year: 2008).*
Orsini, D. A. et al, Aerosol Science and Technology 2008, 42, 343-356. (Year: 2008).*
Jackson. M. L., Journal of the Air Pollution Control Association 1974, 24, 569-575. (Year: 1974).*
Mercer, T. T., Journal of Testing and Evaluation 1978, 6, 9-19. (Year: 1978).*
Greenwald, R. et al, Environmental Science & Technology 2005, 39, 4967-4973. (Year: 2005).*
O'Connell, S., Tum, J., Swanson, S., Boulter, J., "A Novel Approach to Measurement of Atmospheric Fine Siliceous Particulate Matter"; Poster at Joint Assembly of the American Geophysical Union, Montreal, Quebec Canada, May 4, 2015, Abstract AS14A-0003—(1) page.
Tum, J., Fuhrmann, F., Wagner, E., Boulter, J., "Optimizing the Sensitivity of Particulate Silica Quantification by Molybdenum Blue Absorbance Spectrometry"; Poster at UW-Eau Claire Cerca, Eau Claire, WI, Apr. 27-28, 2016—(1) page.

* cited by examiner

REAL-TIME SILICA DISCRIMINATING RESPIRABLE AEROSOL MONITOR WITH PARTICLE SIZER AND PARTICLE GROWTH CHAMBER UPSTREAM OF REAGENT TANK

CROSS REFERENCE TO RELATED APPLICATION

This application claims the benefit of U.S. provisional application 62/654,713 filed Apr. 9, 2018 and hereby corporate by reference.

STATEMENT REGARDING FEDERALLY SPONSORED RESEARCH OR DEVELOPMENT

--

BACKGROUND OF THE INVENTION

The present invention relates generally to monitors for silica dust and in particular to a near-real-time monitor that can distinguish between silica dust and other particulate types.

Crystalline silica dust, specifically the particle size of less than four microns, can evade the body's natural air filtration mechanisms of the nose and throat to embed deep in the lungs where it can promote chronic respiratory diseases such as silicosis, lung cancer, or chronic pulmonary obstructive disease. Such dust can arise in a wide variety of manufacturing environments including construction and demolition, mining and quarry operations, foundries, ceramic, and stone cutting operations and the like. For this reason, the Occupational Safety and Health Administration (OSHA) enforces an exposure limit to less than an average of 50 micrograms per square meter of $SiO_2$ over an eight-hour period.

Typical monitoring requires collection of a sample of airborne particulate matter using a filter for an extended period of time, for example, 8 hours, which is often sent to a remote site for analysis using x-ray diffraction which can identify silica. This process may impose time delays of many days or even weeks limiting the ability to respond promptly to the air quality conditions.

Real time monitoring of dust can be obtained, for example, by measuring scattered light, for example, from a laser, passing through an air sample. While this technique provides rapid assessment of dust, it cannot distinguish between silica dust and other dust types not covered by the regulations and possibly presenting a lower risk. For this reason, the readings provided by such instruments need to be adjusted by an estimate of the percentage of silica in the dust, a task that is problematic to perform accurately in many manufacturing environments and that can significantly affect the accuracy of the measurement.

SUMMARY OF THE INVENTION

The present invention provides an on-site, near-real-time measurement of dust that can accurately identify respirable silica dust concentrations to provide a more accurate measurement of exposure to respirable silica. This improved measurement speed allows prompt remedial action when required while reducing or eliminating false positive measurements.

Specifically then, the present invention in one embodiment provides an airborne silica detection system having a particle sizer for receiving an airstream and preferentially removing particles greater than 4 μm average diameter from the airstream. A reagent tank receives the airstream downstream from the particle sizer and introduces it into a at least one liquid reagent reacting with silica of the particles where a photodetector monitors the reagent tank to detect a change in light caused by the reacting of the silica. An electronic computer executes a stored program held in non-transitory computer readable medium to receive a signal from the photo detector to provide an output indicating silica concentrations over a predetermined amount.

It is thus a feature of at least one embodiment of the invention to provide an automatable method of monitoring silica exposure on an a near real-time basis. By providing a particle sizer, a size-indifferent chemical reaction can be used to quantitatively assess particles relevant to chronic respiratory diseases.

The airborne silica detection system may further include a particle growth chamber receiving the airstream from the particle sizer to increase the individual mass of the particles less than 4 μm in diameter prior to receipt by the reagent tank.

It is thus a feature of at least one embodiment of the invention to improve the sensitivity of the system to extremely fine particles which can be relevant to respiratory disease but which may escape the reagent through percolation out of the reagent.

The predetermined amount may be a density of silicon dioxide of less than 0.1 μg/m$^3$ in the airstream or less than, for example, 40 μg /m$^3$ or 50 μg /m$^3$ in the airstream.

It is thus a feature of at least one embodiment of the invention to provide a system that can make measurements that comport with or exceed current health standards detection requirement.

The at least one reagent provide a chemiluminescent reaction and the photodetector may be a light sensor directed into a reagent reservoir or other mixing volume.

It is thus a feature of at least one embodiment of the invention to provide a detection reaction eliminating the need for sophisticated spectroscopy equipment (for example detecting absorption) that can be difficult to implement and maintain in field conditions where this apparatus is required The at least one reagent may include a molybdate solution and a luminol solution.

It is thus a feature of at least one embodiment of the invention to provide a chemiluminescence reaction providing sufficient detection limits for airborne silica monitoring.

The at least one reagent may provide a buffer for bringing a pH of a silica in solution in the reagent tank within the range of 9 to 11 before or simultaneous to the addition of the molybdate.

It is thus a feature of at least one embodiment of the invention to provide improved sensitivity of the detection system through optimization of reagent pH.

The reagent reservoir or other mixing volume may provide for reflecting surfaces for directing chemiluminescence from the reaction volume to the photodetector. The photodetector may be a photomultiplier tube and may additionally incorporate photon counting electronics.

It is thus a feature of at least one embodiment of the invention to enhance the sensitivity of the detection system buying placement of the measurement signal.

The airborne silica detection may further include a sensor sensing an amount of air received by the reagent tank from the particle growth chamber and providing the signal to the electronic computer for computing silica concentrations.

It is thus a feature of at least one embodiment of the invention to allow normalization of the measurements to varying amounts of air that may be collected by the system to provide a consistent standardized output.

The airborne silica detection system may further include a filter for removing ozone from the airstream before introduction into the reaction chamber. The filter for example may provide services coated with materials reacting with ozone It is thus a feature of at least one embodiment of the invention to reduce or eliminate the effect of side reactions of the chemiluminescence materials with trace atmospheric gases such as ozone.

The particle growth chamber may provide a humidifier creating moisture to the particle growth chamber for condensing on the particles to increase their mass.

It is thus a feature of at least one embodiment of the invention to provide a simple method of increasing the interaction between extremely fine particles and the reagent materials by increasing the mass of the particles for improved integration into the reagent.

The humidifier may be a steam generator.

It is thus a feature of at least one embodiment of the invention to provide a simple method of promoting particle size mass increase through use of fine particles as nucleation sites for saturated moisture.

The particle sizer may provide a cyclonic filter for selectively removing particles greater than 4 µm in diameter and passing other particles to the particle growth chamber.

It is thus a feature of at least one embodiment of the invention to provide a particle sizing device which can provide effective elimination of particles unlikely to be associated with chronic respiratory diseases before they undergo reaction and subsequent measurement.

The airborne silica detection may include a cartridge providing at least two compartments holding reagents for use in the reagent tank and at least one compartment for receiving waste reagent from the reagent tank and the airborne silica detection system may provide pumps controlled by the controller for moving the reagents and waste to and from the reagent tank respectively.

It is thus a feature of at least one embodiment of the invention to provide an effective method of managing cleaning the reagent tank in the field in order to implement multiple automatic measurement cycles through the use of replaceable prefilled cartridges.

The cartridge may further provide a compartment receiving particles filtered by the particle filter collected from the particle filter.

It is thus a feature of at least one embodiment of the invention to provide for a simple disposal and sequestration mechanism for filtered particles that can reduce interference in subsequent measurements.

The cartridge may further provide at least one compartment holding rinsing water and for receiving wastewater and the airborne silica detection system may further provide a rinse line providing water from the cartridge to the reagent tank and a drain line moving liquid from the reagent tank to the cartridge and wherein the electronic computer executes the stored program to automatically drain and rinse the reagent tank for repeated measurements.

It is thus a feature of at least one embodiment of the invention to permit automatic cleaning of the reagent tank in between used to permit multiple successive measurements on a near real-time basis.

These particular objects and advantages may apply to only some embodiments falling within the claims and thus do not define the scope of the invention.

DETAILED DESCRIPTION OF THE PREFERRED EMBODIMENT

Figure 1:
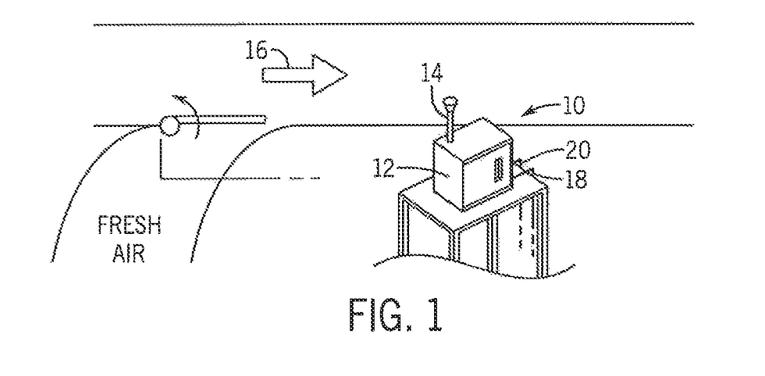
FIG. 1 is a perspective view of a monitoring station using the present invention positioned in the path of generated dust.

Referring now to FIG. 1, the present invention provides an on-site, real-time silica dust monitoring system 10 that may be used indoors, for example, attached to the air circulation equipment of the building, or outdoors, for example, placed in the flow path 16 of air passing through dust-generating activities such as mining or the like (as shown). The monitoring system 10 may provide for a housing 12 having an air sampling inlet 14 positioned in the dust flow path 16. The monitoring system 10 may receive electrical power, for example, through power lines 18 and may communicate data through a network connection 20 or wirelessly as discussed below.

Figure 2:
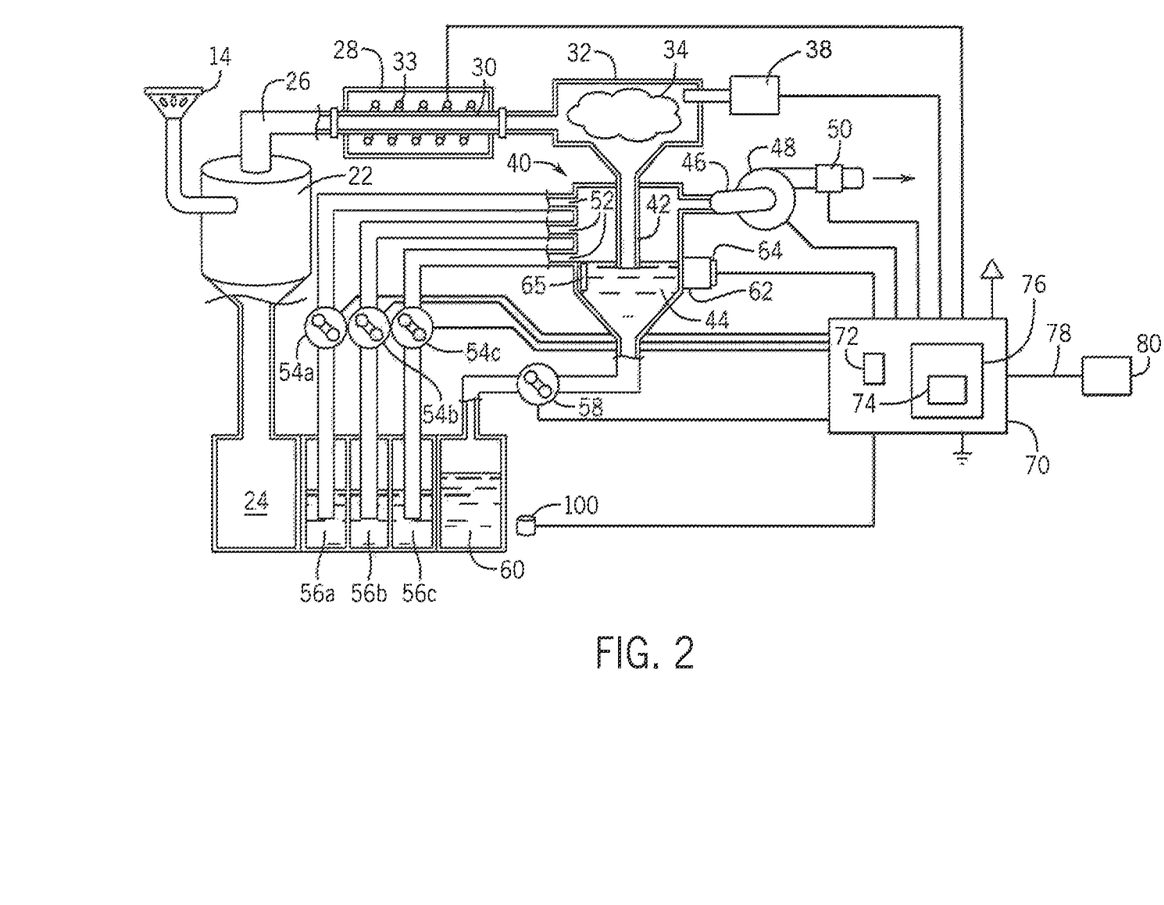
FIG. 2 is a block diagram of the present invention showing the various components as controlled by a microcontroller.

Referring now to FIG. 2, the air sampling inlet 14 may lead to a cyclone separator 22 of conventional design performing a size selection on the particles in received air based on a defined cutpoint that allows passage of smaller particles and rejection/collection of larger particles. In an example with a cutpoint of 4 microns, cyclone separator 22 preferentially rejecting particles larger than 4 microns into a waste collection hopper 24 and allowing air holding particles of smaller size to pass through flow tube 26. Desirably, the cyclone separator 22 will allow passage of particles having an average diameter in a range from 0.1 to 4 µm and will reject 70% of particles larger than 4 µm and preferably 90% of the particles larger than 5 µm.

Air and dust particles exiting the diffusion denuder 28 may then optionally passed into a steam jet aerosol particle growth system 32 providing a supersaturated steam atmosphere 34 produced by a steam generator 38. Smaller particles much less than four microns serve as nucleation sites for the supersaturated steam which condenses onto their surface, increasing the mass of fine particles and increasing their collection within the reaction chamber 40 and interaction with the reagents contained therein. In this regard, the increased mass of the particles tends to prevent them from percolating out of the solution before reaction and the water coating may improve their wetting and thus integration into the contained reagent.

Air and dust particles exiting the diffusion denuder 28 may then optionally passed into a steam jet aerosol particle growth system 32 providing a supersaturated steam atmosphere 34 produced by a steam generator 38. Smaller particles much less than four microns serve as nucleation sites for the supersaturated steam which condenses onto their surface, increasing the mass of fine particles and increasing their collection within the reaction chamber 40 and interaction with the reagents contained therein. In this regard, the increased mass of the particles tends to prevent them from percolating out of the solution before reaction and the condensed water coating may increase their masses and thus integration into the collection reagent.

An outlet from the steam jet particle growth system 32 passes through an impinger tube 42 extending vertically downward into the reaction chamber 40 to a point beneath the surface of a reaction medium 44 (being an aqueous solution of reactants to be described below) in the reaction chamber 40 serving to retain the dust particles as air and dust particles bubble through the reaction medium 44 to exit an exhaust port 46 in a wall of the reaction chamber 40 drawn by air pump 48. The outlet of air pump 48 may provide for a flowmeter 50 so that a predetermined volume of air and particulates can be percolated through the reaction medium 44 for each given measurement. Generally, the flowmeter 50 may be a mass flowmeter or may be a volume flowmeter with pressure gauge intended to provide an approximation of the total mass of airstream received by the reaction medium 44.

The reaction chamber 40 provides introduction ports 52 connected through respective pumps 54a, 54b, and 54c (for example, peristaltic pumps) with corresponding water container 56a and reagent reservoirs 56b and 56c so that water and reagents can be introduced into the reaction chamber 40.

A drain pump 58 may communicate with the bottom of the reaction chamber 40 to drain liquid from that reaction chamber 40 into a waste receptacle 60.

The reaction chamber 40 may include a window and associated collection optics, for example, a collection lens and filter 62 and opposing reflector 65, to collect light within the volume of the reaction medium 44 for measurement by a photomultiplier 64. In this way, silica in the reaction medium 44 may react with the reagents from reservoirs 56b and 56c, and the light so produced may be measured for determination of the mass of silica. The reflector 65 may be a discrete mirror or the entire reaction chamber 40 may be reflective in a way intending to collect light for receipt by the photo multiplier 64. The filter may have a bandpass characteristic centered around the frequency of the chemical luminescence (e.g. 445 nanometers) to reject external light. Alternatively, or in addition, the reaction chamber 40 may be sealed against light.

Each of the heater 33, the steam generator 38, the air pump 48, the mass flowmeter 50, the pumps 54 and 58, and the photomultiplier 64 may communicate with an electronic controller 70 providing a processor 72 that may execute a stored program 74 contained in computer memory 76 as will be discussed below. The controller 70 may also include interface circuitry, for example, an A/D converter or counter associated with the photomultiplier 64 and various solid-state relays or switches for controlling power to the various other components described.

The controller 70 may communicate with signal lines 78 which may connect to a network or to a wireless communication device 80 for communication of data to and from the controller 70.

Figure 3:
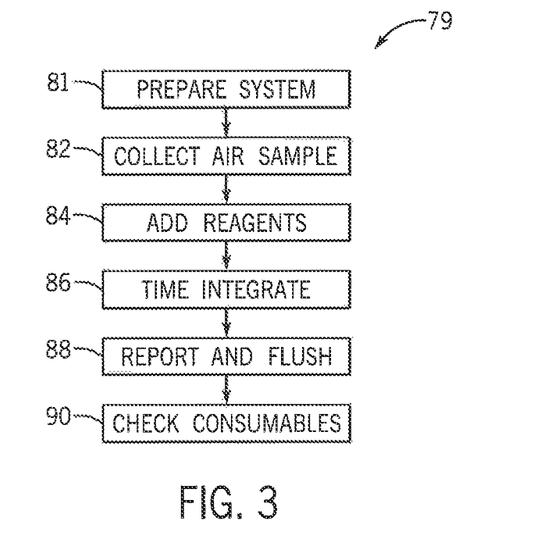
FIG. 3 is a flowchart showing the principal steps of an exemplary program executed by the microcontroller in one embodiment the present invention.

Referring now to also to FIG. 3, the program 74 may operate to prepare to collect a sample of air and dust as indicated by process block 81. This process involves heating up the heater 33 (if used) and the steam generator 38 (if used) and filling the reaction chamber 40 with a predetermined volume of aqueous reagents using pump 54b.

Once proper conditions have been obtained, the air pump 48 is activated for a period of time to draw a predetermined volume of air through the system to begin the collection of an air sample as indicated by process block 82. The predetermined volume of air may be determined by measuring the actual mass or volume of air to draw a predetermined amount air through the system using the flowmeter 50.

Particles sized in the cyclone separator 22 are drawn by the air pump 48, through the diffusion denuder 28 to remove gaseous interferences and into the steam jet particle growth chamber 34, followed by particle collection and subsequent reaction in the reagent liquid by means of the impinger 42. A sampling cycle, for example, may involve between 20 minutes to one hour of sampling time at five liters per minute airflow.

After the air and dust sample has been completed, the air pump 48 may be turned off. At this point, as indicated by process block 84, reagents may be added to the reaction medium 44 using pumps 54b and 54c to promote chemiluminescence in proportion to the silica contained in the sampled air volume.

In particular, the reaction medium 44 in reservoir 56b during the collection of the air sample of process blocks 62 may be a molybdate solution that combines with the silica to form a heteropoly acid (HPA). The HPA is then reduced using the reagent in container 56c (added during process block 84) which may be a luminol solution (3-Aminophthalhydrazide, 5-Amino-3-dihydro-1,4-phthalazinedione) which reacts with the HPA to produce a quantitative amount of light at 445 nanometers. The result is a chemical luminescence that can be used to derive a mass of silica involved in the reaction. The inventors have determined that sensitivity can be increased by control of the pH of the solution receiving the silica to a value of 10 and ideally within a range from 9 to 11 before the introduction of the molybdate. The inventors have determined that the limit of detection for silicate is approximately 30 ng with a signal to noise ratio of four.

As indicated by process block 86, light received from the reaction medium 44 by the photomultiplier 64 may be integrated, for example, for a predetermined time interval after the introduction of the reagents or according to threshold levels based on the maximum light output during a predetermined period. This integrated value is then provided to the controller 70 which may, for example, apply the empirically derived table to the measurement to output the total mass of silica within the air sample for the particular sensitivity of the photomultiplier 64 and the optical system. Preferably, the signal from the photomultiplier 64 and knowledge of the airflow mass from sensor 50 are used to establish a density of $SiO_2$ within the air to provide an alarm if this density exceeds 50 µg /m$^3$ or over 25 µg/m$^3$. As indicated by process block 88, this information may immediately be reported or may form the basis of alarm or may implement automatic control measures, for example, increasing air filtration for indoor locations or introducing fresh filtered air into an interior workspace. During this reporting process, pump 58 may be activated to flush the reaction chamber 40 in preparation for the next measurement. An additional water rinse of the reaction chamber 40 may then be performed to remove trace amounts of the silica and reactants, using for example, water in an additional reservoir 56a

Referring again to FIG. 2, each of the reservoirs 56 and 60 and waste collection hopper 24 may be integrated into a single container to provide a ready replacement of the consumables and disposal of the waste of this process. Alternatively, separate containers may he provided for the consumables and the waste material. A sensor 100 may detect the presence of the container and/or levels of liquid in the container to provide the controller 70 with information about the same. Referring to process block 90 of FIG. 3, at the conclusion of each measurement cycle, sensors 100 may be interrogated to provide information about the need to replace any consumables or to empty the waste collection hopper 24 or receptacle 60. Following these steps, the program 74 may loop back to step 82 in order to monitor the air quality in a semi-continuous manner.

Figure 4:
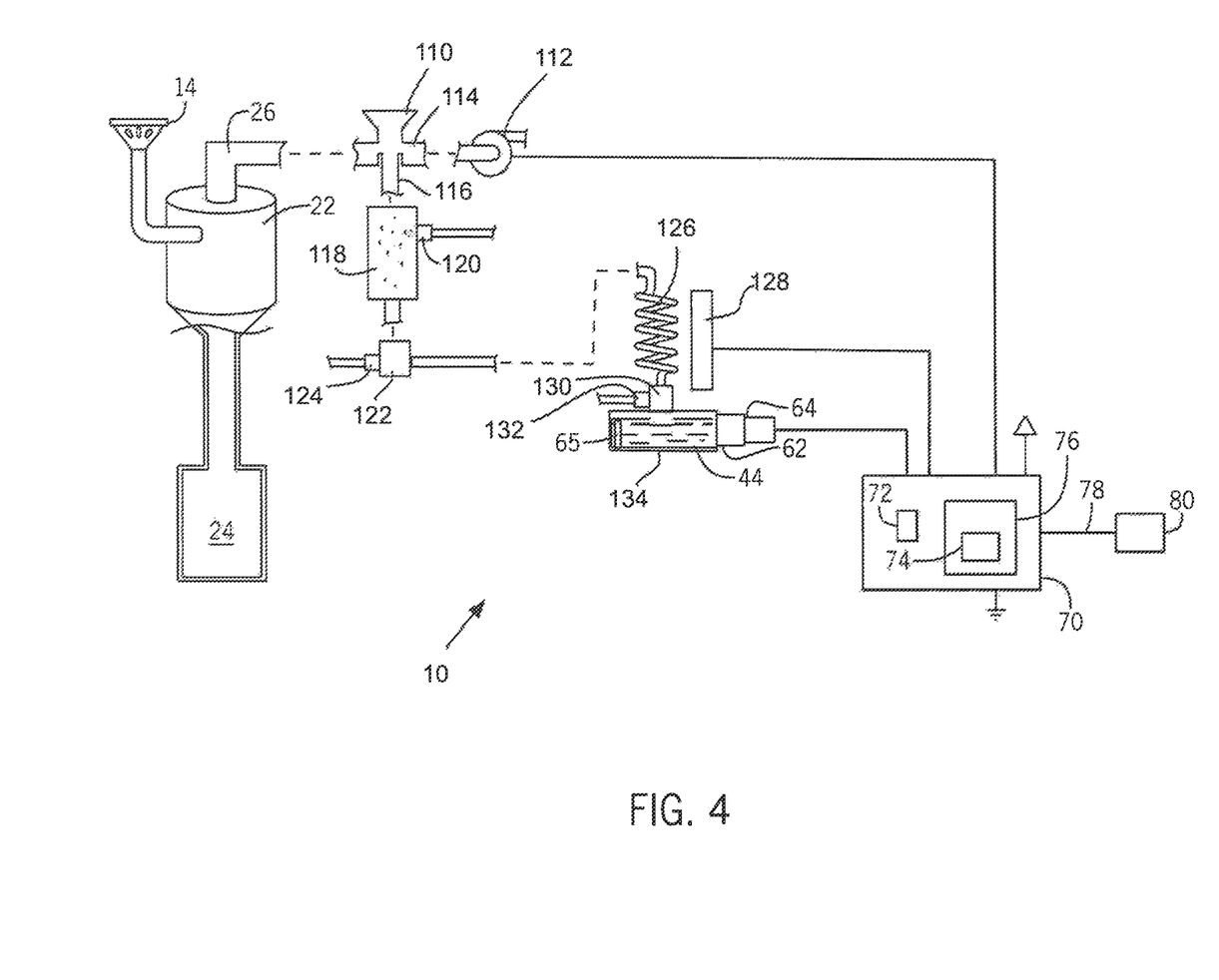
FIG. 4 is a block diagram of a variant of the present invention showing the various components as controlled by a microcontroller.

Referring now to FIG. 4, in another example, the real-time silica dust monitoring system 10 is configured to continuously monitor the air quality. This real-time silica dust monitoring system 10 is substantially similar to that shown in FIG. 2, only differs in the following ways in order to achieve continuous monitoring. A virtual impactor 110 and an air pump shown as vacuum pump 112 are incorporated downstream of the cyclone separator 22 instead of diffusion denuder 28. The virtual impactor 110 performs a second stage of size selection, with the cyclone separator's 22 cutpoint corresponding to the first stage of size selection and the virtual impactor's 110 cutpoint corresponding to the second stage of size selection. Two exit tribes 114, 116 extend from the virtual impactor 110 and separate the gas flow of the virtual impactor into a major flow that is removed through exit tube 114 by the vacuum pump 112 and a minor flow that flows through exit tube 116 and continues downstream through the real-time silica dust monitoring system 10. Within the virtual impactor 110, particles with diameters greater than the virtual impactor's 110 cutpoint are entrained in and flow with the minor flow whereas the particles with diameters that are smaller than virtual impactor's 110 cutpoint along with the remainder of the flowing gas define the major flow that are pulled into the vacuum pump 112. By incorporating the virtual impactor 110 the diffusion denuder 18 may be eliminated as unnecessary in this example because the relative concentration of gaseous oxidizers will be reduced as the particle concentration is increased. Furthermore, concentration the particles by a factor of up to a multiple of 10 may be achieved by the splitting and reduction of the gas flow. In this way, the combination of the cyclone separator 22 and the virtual impactor 110 selects a "slice" of particles of interest: those small enough to be respirable and those large enough to substantially contribute to the silica mass.

Still referring to FIG. 4, instead of an impinger tube 42, an aerosol collector 118 is provided, such as an Aerosol Counterflow Two-Jet Unit (ACTJU) aerosol collector, developed by Pavel Mikuška at the institute of Analytical Chemistry of the Academy of Sciences in the Check Republic. In the aerosol collector 118, airborne particles are transferred continuously into a small flow rate of water or other aqueous solution from a solution delivery inlet 120. A reagent flow mixer 122 that receives reagent through a reagent inlet 124, a mixing tube shown as helical mixing tube 126, a heater 128, and luminol reagent mixer 130 that receives a luminol reagent through reagent inlet 132 are arranged downstream of the aerosol collector 118 and upstream of a reaction flow cell 134. Reaction flow cell 134 has a window and associated collection optics, which may be similar to those shown in FIG. 2 and may include a reflective surface of the reaction flow cell 134 or a reflector 65, collection lens and filter 62, photomultiplier tube such as photomultiplier 64, along with photon counting electronics, which include various photon counting units and other photon counting products available from, for example, Hamamatsu Photonics, Boston Electronics, or the like.

Still referring to FIG. 4, after the airborne particles are transferred continuously into the small flow of water or other aqueous solution in the aerosol collector 118, it flows into the reagent flow mixer 122 to mix with the reagent from reagent inlet 124. The first reagent mixed with the aerosol collector's 118 liquid flow in the reagent flow mixer 122 is a molybdate solution that combines with silica at an appropriate pH to form an HPA (heteropoly acid), which then flows into the helical mixing tube 126. The reaction occurring in the helical mixing tube 126 is performed for an optimized period of time determined by the flow rate of liquid through the aerosol collector 118 and the length of the helical mixing tube 126. The mixed liquid/reagent flow passing through the helical mixing tube 126 flows at a rate that provides a residence time within the helical mixing tube 126 that is adequate to complete the reaction. The temperature of this reaction may also be controlled by way of heater 128 to ensure completion of the reaction. This fully reacted mixture exits the helical mixing tube 126 and flows into the luminol reagent mixer 130 to mix with a chemiluminescence or luminol reagent. Accordingly, in the luminol reagent mixer 130, the HPA is subsequently reduced by mixing with the luminol reagent, such as 3-Aminophthalhrydrazide, 5-Amino-2,3-dihydro-1,4-phthalazinedione, which is delivered through reagent inlet 132 and reacts with the HPA to produce a quantitative amount of light at, for example, 445 nanometers. Because this reaction is rapid, this mixing is done or completed in the reaction flow cell 134 that is viewed by the light detection system incorporating photomultiplier tube 64 and photon counting electronics. In the flow cell 134, the light produced may be collected by way of the photon counting electronics and completely and measured for the determination of the mass of silica.

Still referring to FIG. 4, in this example of a continuously operating real-time silica dust monitoring system 10, particles are continuously transferred and concentrated into solution so that they are undergoing chemical transformations to produce light continuously rather than in batches. Instead of accumulating particles in suspension prior to batch chemical reaction like described with respect to FIG. 2, the chemical reaction occurs continuously, and the photon counts (light) is accumulated electronically. Since continuous measurements are made in this example, the air and reaction solutions are correspondingly pumping continuously. No airflow amounts need to be determined since the instrument(s) sense how often it may report a value based on the signal-to-noise ratio as photon counts accumulate. Nor is rinsing or flushing required for subsequent measurements due to the continuous nature of the measurement. The virtual impactor 110 and the capture of particles into the liquid phase can be done efficiently in a much smaller volume compared to the system shown in FIG. 2. Although the response time should not be substantially altered, the system of FIG. 4 can allow for more easily variable control because the photons resulting from the chemistry are counted continuously. Thus, the instrument control system can determine how long to collect light in order to have an adequate signal-to-noise ratio to insure quantification of silica particles. Due to the continuous nature of the measurement, the instrumentation may be simpler than in systems that require time-varying control procedures intrinsic to batch mode measurements.

Certain terminology is used herein for purposes of reference only, and thus is not intended to be limitinge. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

What we claim is:

1. An airborne silica detection system comprising:
   a particle sizer for receiving an airstream and preferentially removing particles greater than 4 μm average diameter from the airstream;
   a reagent tank having an inlet and an outlet for receiving and discharging the airstream respectively, the reagent tank adapted to contain at least one liquid reagent at a reagent height below the outlet within the reagent tank and receiving the airstream downstream from the particle sizer through the inlet to a nozzle positioned below the outlet, to bubble the airstream through the at least one liquid reagent when so contained so that at least one liquid reagent may react with silica of the particles;
   a photodetector positioned adjacent a sidewall of the reagent tank at a position lower than the outlet, the photodetector monitoring the reagent tank to detect a change in light caused by the reacting of the silica;
   a particle growth chamber receiving the airstream from the particle sizer to increase the individual mass of the particles less than 4 μm in diameter prior to receipt by the reagent tank to increase capture of the particles in the at least one liquid reagent during the bubbling of the airstream through the at least one liquid reagent when so contained;
   a flow sensor sensing an amount of air received by the reagent tank from the particle growth chamber; and
   an electronic computer executing a stored program held in non-transitory computer readable medium to receive a signal from the photodetector and the flow sensor to provide an output upon silica concentrations in the airstream rising above a predetermined threshold;
   an air pump for moving the airstream along a path through the particle sizer, the particle growth chamber, the flow sensor, and the reagent tank.

2. The airborne silica detection system of claim 1 wherein the predetermined threshold is a non-zero concentration of silicon dioxide of less than 0.1 μg/m$^3$ in the airstream.

3. The airborne silica detection system of claim 1 wherein the predetermined threshold is a non-zero density of silicon dioxide less than 40 μg/m$^3$ in the airstream.

4. The airborne silica detection system of claim 1 further including the at least one liquid reagent and wherein the at least one liquid reagent provides a chemiluminescent reaction and the photodetector is a light sensor directed into the reagent tank.

5. The airborne silica detection system of claim 4 wherein the at least one liquid reagent includes a molybdate solution and a luminol solution.

6. The airborne silica detection system of claim 5 further including a pump and wherein the electronic computer further controls the pump for the addition of the molybdate solution to the reagent tank and wherein the at least one liquid reagent provides a solution other than the molybdate solution providing a buffer for bringing a pH of the silica in solution in the at least one liquid reagent of the reagent tank within the range of 9 to 11 before the addition of the molybdate solution.

7. The airborne silica detection system of claim 4 wherein the reagent tank provides for reflecting surfaces for directing chemiluminescence from the reagent to the photodetector.

8. The airborne silica detection system of claim 7 wherein the photodetector is a photomultiplier tube.

9. The airborne silica detection system of claim 1 further including a filter for removing ozone from the airstream before introduction into the reagent tank.

10. The airborne silica detection system of claim 9 wherein the filter provides surfaces coated with materials reacting with ozone.

11. The airborne silica detection system of claim 1 wherein the particle growth chamber provides a humidifier providing moisture to the particle growth chamber for condensing on the particles to increase their mass.

12. The airborne silica detection system of claim 11 wherein the humidifier providing moisture to the particle growth chamber is a steam generator.

13. The airborne silica detection system of claim 1 wherein the particle sizer is a cyclonic filter for selectively removing particles greater than 4 μm in diameter and passing other particles to the particle growth chamber.

14. An airborne silica detection system comprising:
    a particle sizer for receiving an airstream and preferentially removing particles greater than 4 μm average diameter from the airstream;
    a reagent tank having an inlet and an outlet for receiving and discharging the airstream respectively, the reagent tank adapted to contain at least one liquid reagent at a reagent height below the outlet within the reagent tank and receiving the airstream downstream from the particle sizer through the inlet to a nozzle positioned below the outlet, to bubble the airstream through the at least one liquid reagent when so contained so that at least one liquid reagent may react with silica of the particles;

a photodetector positioned adjacent a sidewall of the reagent tank at a position lower than the outlet, the photodetector monitoring the reagent tank to detect a change in light caused by the reacting of the silica;

a particle growth chamber receiving the airstream from the particle sizer to increase the individual mass of the particles less than 4 μm in diameter prior to receipt by the reagent tank to increase capture of the particles in the at least one liquid reagent during the bubbling of the airstream through the at least one liquid reagent when so contained;

a flow sensor sensing an amount of air received by the reagent tank from the particle growth chamber;

an electronic computer executing a stored program held in non-transitory computer readable medium to receive a signal from the photodetector and the flow sensor to provide an output indicating silica concentrations in the airstream over a predetermined amount;

an air pump for moving the airstream along a path through the particle sizer, the reagent tank, the particle growth chamber, and the flow sensor; and further including a cartridge providing at least two compartments holding reagents for use in the reagent tank and at least one compartment for receiving waste reagent from the reagent tank and wherein the airborne silica detection system provides pumps controlled by the electronic computer executing the stored program for moving the reagents and waste to and from the reagent tank respectively.

15. The airborne silica detection system of claim 14 wherein the cartridge further provides a compartment receiving particles removed by the particle sizer.

16. The airborne silica detection system of claim 14 wherein the cartridge further provides at least two compartments, a first compartment holding rinsing water and a second compartment for receiving wastewater and further including a rinse line providing water from the first compartment of the cartridge to the reagent tank and a drain line moving liquid from the reagent tank to the second compartment of the cartridge and wherein the electronic computer executes the stored program to automatically drain and rinse the reagent tank for repeated measurements.

* * * * *